United States Patent [19]

Fischer

[11] Plant 4,976

[45] Jan. 18, 1983

[54] AFRICAN VIOLET NAMED EVENING STAR

[75] Inventor: Arnold W. Fischer, Hanover, Fed. Rep. of Germany

[73] Assignee: Pan American Plant Company, Parrish, Fla.

[21] Appl. No.: 252,318

[22] Filed: Apr. 9, 1981

[51] Int. Cl.[3] ..... A01H 5/00

[52] U.S. Cl. ..... Plt./69

[58] Field of Search ..... Plt./69

*Primary Examiner*—James R. Feyrer

*Attorney, Agent, or Firm*—Chas. W. Rummler

[57] ABSTRACT

A new African Violet plant distinguished by its profuse production of star-shaped flowers of a pleasing violet color, borne as in a bouquet above the medium green foliage of the plant, and by its vigorous, compact rosette-shaped growth habit.

4 Drawing Figures

BACKGROUND OF THE NEW PLANT

My new African Violet variety herein described originated as a seedling of unknown parentage grown in my breeding facilities at Hanover, West Germany. This plant was discovered by me among my breeding stock in 1975 and was selected by me for testing because of its profuse production of flowers having a pleasing violet color in the middle violet range borne high above the foliage on strong, upright stems. This new plant was reproduced by me by means of cuttings in my greenhouse at Hanover and subsequently this plant was propagated through a series of generations by means of cuttings, which demonstrated that the novel characteristics of the new plant would hold true from generation to generation and appeared to be firmly fixed. Commercial propagation of this new plant is now being done at West Chicago, Ill., and at Palma Sola, Fla., U.S.A., by means of leaf cuttings.

DESCRIPTION OF THE DRAWINGS

This new violet plant is illustrated by the accompanying drawings, of which sheet 1 is a photographic view of a potted plant in full bloom, sheet 2 is a photographic print showing a full face view of flower of this variety which has been hand-painted to show the true flower color, and sheets 3 and 4 are prints of machine copies of the front and back sides, respectively, of typical leaves of this plant.

DESCRIPTION OF THE NEW PLANT

The following is a detailed description of the new plant based upon observations made in greenhouse at West Chicago, Ill., U.S.A., the color designations being according to The R.H.S. Colour Chart published by The Royal Horticultural Society of London, England.

THE PLANT

Origin: Seedling.
Parentage: Unknown.
Classification:
- *Botanic.*—*Saintpaulia ionantha.*
- *Commercial.*—Potted African Violet.

Form: Compact and rosette shaped.
Growth: Vigorous and strong.
Growth rate: Rapid.
Foliage:

- *Quantity.*—Abundant. About 28 leaves.
- *Size of leaf.*—Length — From insignificant to about 70 mm. Width — From insignificant to about 68 mm.
- *Shape of leaf.*—Oval with obtuse to rounded tip, cordate base, and repand margin.
- *Texture.*—Pubescent.
- *Aspect.*—Glossy.
- *Ribs and veins.*—Pinnate and very prominently displayed on the under side of the leaves.
- *Color.*—Upper Side — 137A. Under Side — 138D at the edge, fading into 66C in the center of the leaf.
- *Petioles.*—Length — Insignificant to about 80 mm.

THE BUD

Form: Globular.
Size: Average with various lengths and diameters at time of opening.
Opening rate: Typical violet.
Color of petals: When sepals divide and petals begin to unfurl — 84A.
Sepals:
- *Number.*—Five.
- *Shape.*—Lanceolate and branched, becoming flat when flowers open.
- *Color.*—Inside — 199A. Outside — 165A.

Calyx:
- *Size.*—Small.
- *Shape.*—Calyx splits to star shape.
- *Aspect.*—Hairy.

Flower stem:
- *Length.*—From insignificant to about 100 mm.
- *Aspect.*—Hairy.
- *Strength.*—Rigid and erect.
- *Color.*—146C.

THE FLOWER

Blooming habit: Intermittent.
Flowering: Profusely.
Size of flower: Medium.
- *Diameter.*—About 30 to 40 mm.

Borne: As a cyme.
Shape: Cup-shaped when bloom first opens, becoming flat as the bloom matures.
Petalage:
- *Number of petals.*—Five in sympetalous arrangement.

*Form.*—Rotate and actinomorphis with rounded apex and repand margin.

*Texture.*—Soft.

*Aspect.*—Satiny.

*Color.*—Upper Surface — 84A. Reverse Surface — 84D.

Petaloids:

*Number.*—None to a few.

Flower stem:

*Character.*—Strong and upright.

*Length.*—From insignificant to about 100 mm.

*Color.*—146C.

Persistence: The flowers hang on and dry.

Fragrance: None.

Lasting quality:

*On the plant.*—From 10 to 20 days.

REPRODUCTIVE ORGANS

Stamens:

*Anthers.*—Five in number and in monadelphous arrangement. Size: Varies. Color: Yellow.

*Filaments.*—Length: About 3 mm. Color: Whitish yellow.

*Pollen.*—Color — Yellow.

Pistils:

*Number.*—One.

*Style.*—Length: About 5 mm. Color: 84A.

*Stigma.*—Color — Whitish.

Ovaries: Hypogynous and tomentose.

This new African Violet cultivar is distinguished by its profuse production of star-shaped flowers having a pleasing violet color in the middle violet range and borne as a bouquet above the medium green foliage of the plant. This new variety is also distinguished by its vigorous growth habit and the excellent keeping quality of its flowers.

I claim:

1. A new and distinct African Violet plant, substantially as herein shown and described, characterized by its profuse production of rotate actinomorphic flowers, having a pleasing violet color, borne in a bouquet above the plant foliage.

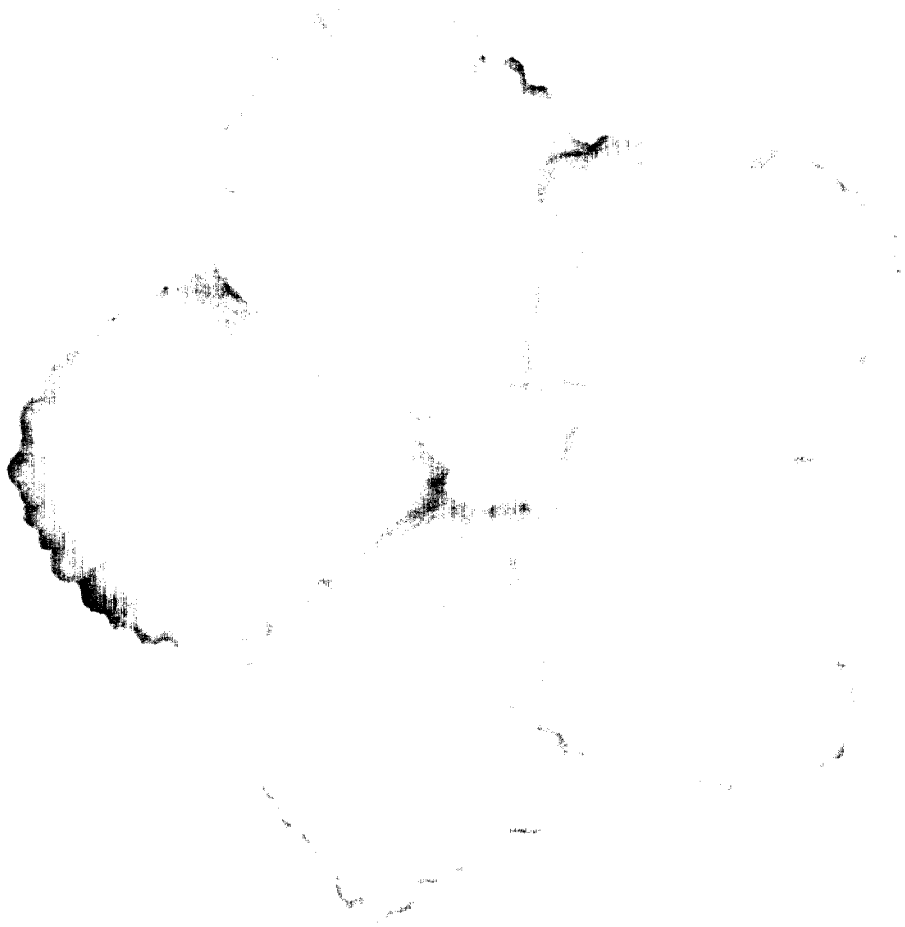

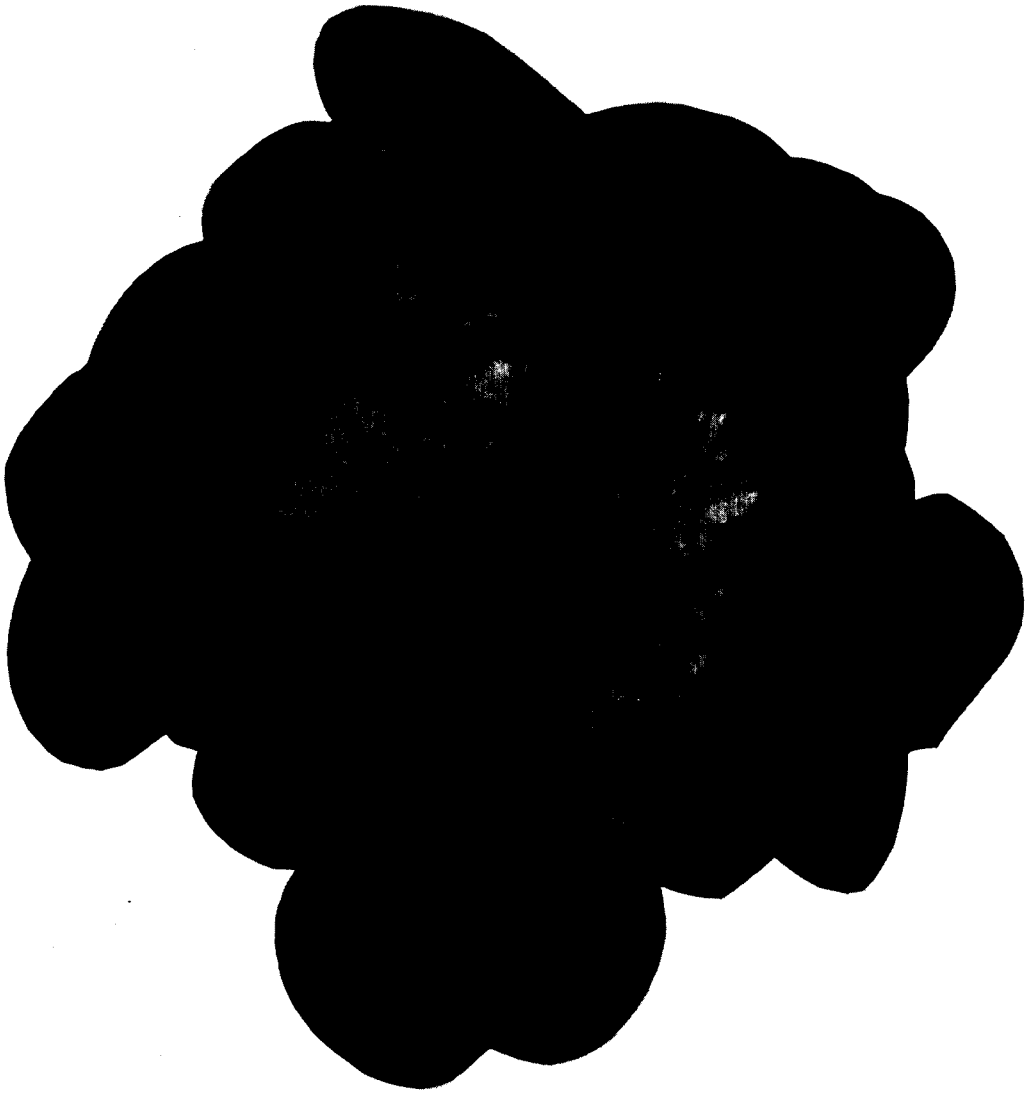

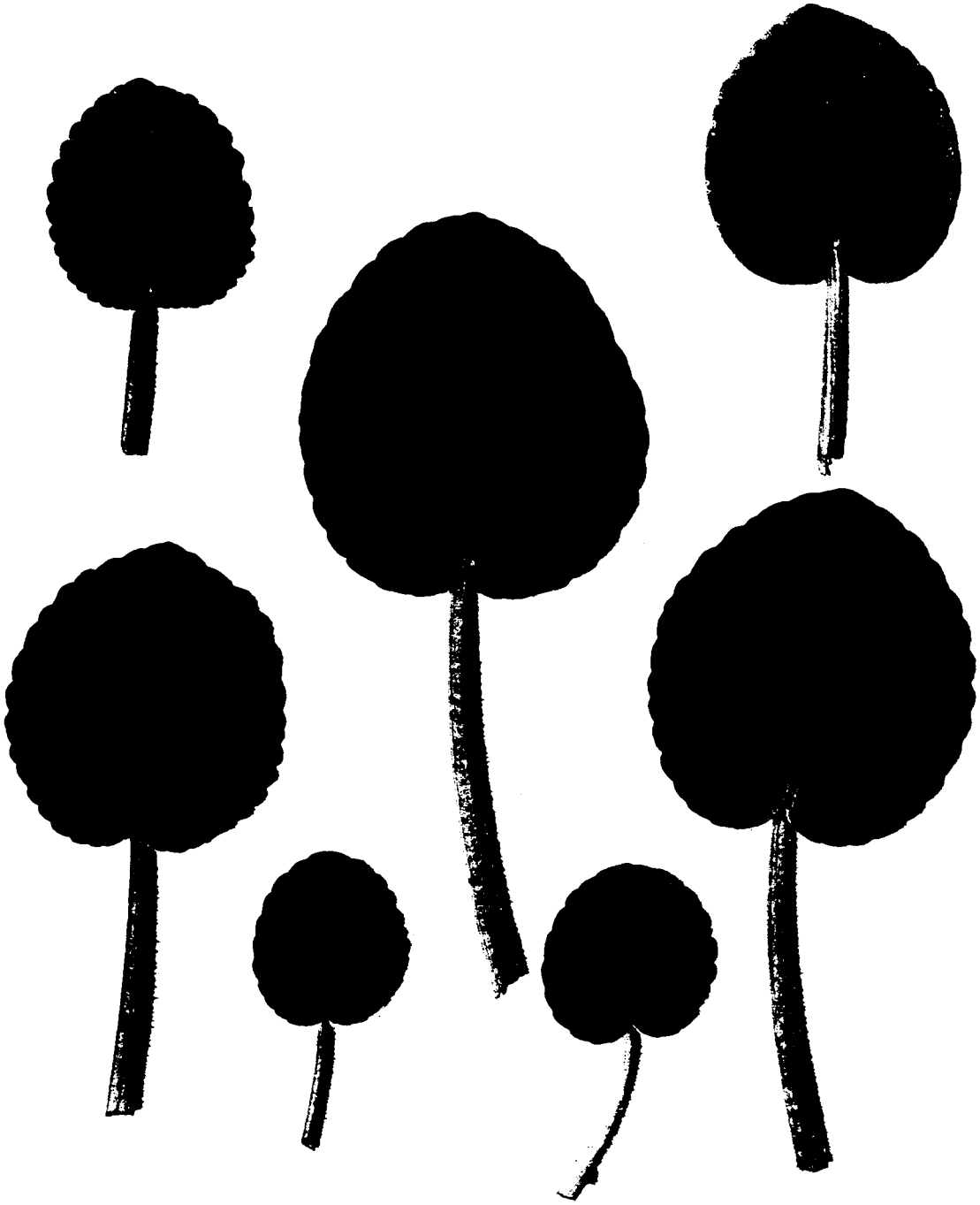

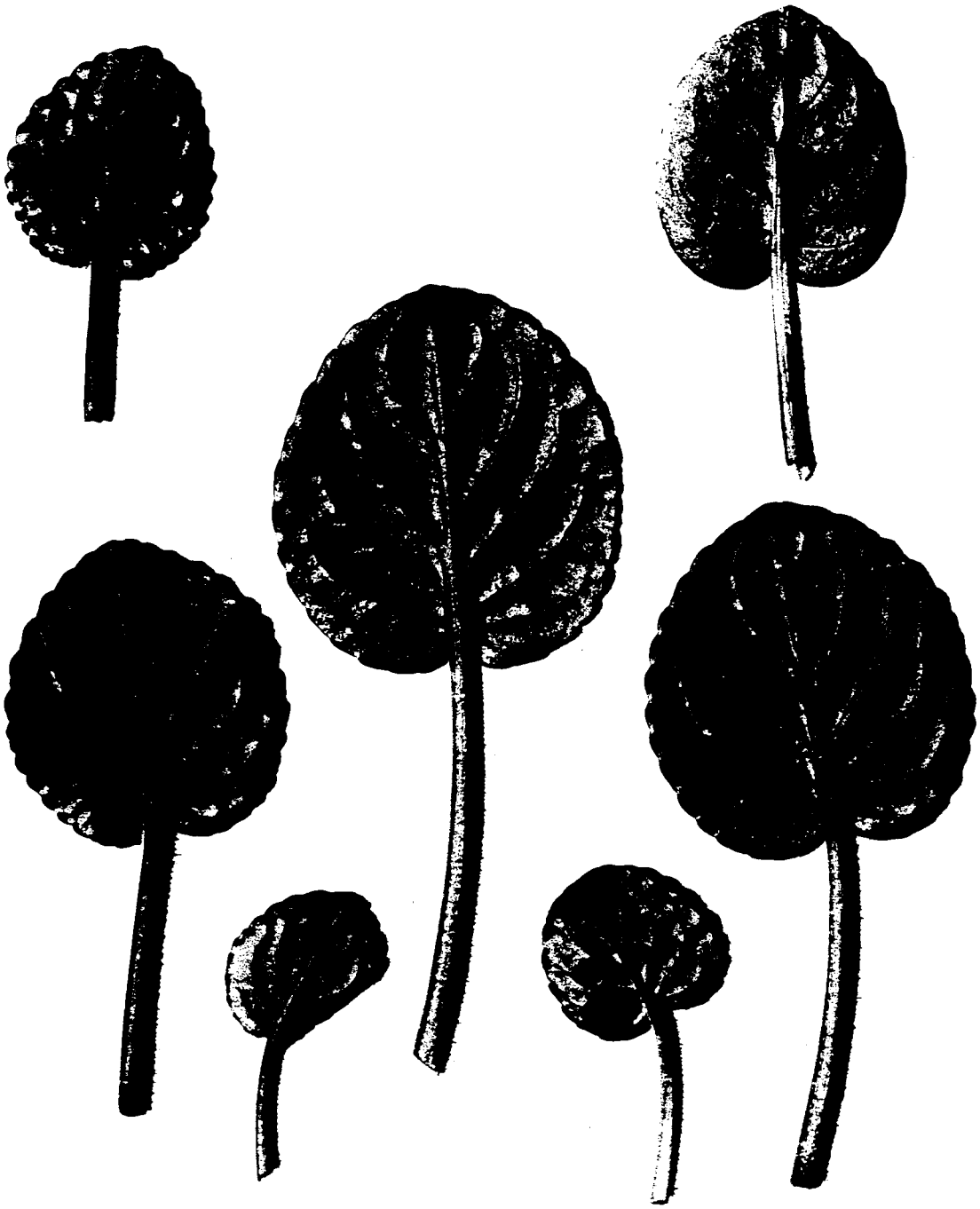

* * * * *